US005637107A

United States Patent [19]

Vaillancourt

[11] Patent Number: 5,637,107

[45] Date of Patent: Jun. 10, 1997

[54] STERILIZED VIAL CLOSURE AND A STERILIZED PARENTERAL VIAL

[76] Inventor: Vincent L. Vaillancourt, 14 Bunyan Dr., Livingston, N.J. 07039

[21] Appl. No.: 365,707

[22] Filed: Dec. 29, 1994

[51] Int. Cl.$^{6}$ .......... A61B 19/00

[52] U.S. Cl. .......... 604/403; 604/411; 604/414; 604/415; 604/88; 604/199; 604/201; 604/265; 604/905

[58] Field of Search .......... 604/415, 411, 604/412, 403, 80, 88, 199, 201–208, 265–267, 905, 414

[56] References Cited

U.S. PATENT DOCUMENTS

| | | | |
|---|---|---|---|
| 1,189,465 | 7/1916 | Mayo | 604/415 |
| 2,020,828 | 11/1935 | Goldberg | 604/201 |
| 2,573,637 | 10/1951 | Bender | 604/403 |
| 3,306,563 | 2/1967 | Soto | 604/413 |
| 4,308,232 | 12/1981 | Crouther et al. | 604/403 |
| 4,559,043 | 12/1985 | Whitehouse et al. | 604/201 |
| 5,232,687 | 8/1993 | Geimer | 424/45 |
| 5,290,254 | 3/1994 | Vaillancourt | 604/192 |
| 5,334,178 | 8/1994 | Haber | 604/415 |
| 5,478,328 | 12/1995 | Silverman et al. | 604/272 |

*Primary Examiner*—John G. Weiss

*Assistant Examiner*—Bruce E. Snow

*Attorney, Agent, or Firm*—McAulay, Fisher, Nissen, Goldberg & Kiel, LLP

[57] ABSTRACT

The exposed surface of the bung closing off the glass vial of medicament is provided with a permanent contact bactericide coating to prevent microbial growth. The coating is applied by a vapor deposition process. Upon removal of a pull tab on a cap securing the bung to the glass vial, the exposed bactericide containing surface of the bung can be pierced by a needle in order to obtain access to the medicament in the vial.

18 Claims, 1 Drawing Sheet

STERILIZED VIAL CLOSURE AND A STERILIZED PARENTERAL VIAL

This invention relates to a sterilized vial closure and a sterilized parenteral vial.

As is known, various types of parenteral vials have been employed as containers for medicaments which can be maintained in a sealed condition until ready for use. For example, one such vial is formed of a glass container having an opening at one end with a rubber bung disposed in the opening in order to seal the medicament within the container. In addition, an aluminum cap has been secured to the glass vial over the rubber bung in order to maintain the bung in a secured position within the glass vial. Typically, after the glass vial has been filed with a medicament and the rubber bung pushed into place, the assembly is subjected to a sterilization treatment, for example, a steam sterilization treatment followed by capping or placing and securement of the aluminum cap to the glass vial. However, it has been found that droplets of water may form and be deposited on the rubber bung during the steam sterilization process. Subsequently, during the time that these droplets evaporate, microbial growth may occur and thereby contaminate the surface of the bung which has been covered with the aluminum cap. Consequently, when the cap is removed or when a pull tab on the cap has been removed to expose the rubber bung, so that a needle may pass through the bung to gain access to the medicament within the vial, contamination has already occurred.

Another concern with vials of the above type is that when the pull tab is removed in order to expose the rubber bung to the environment, the user may accidentally touch or brush against the exposed surface of the bung thereby contaminating the bung.

In cases where vials having rubber bungs have been left exposed for a time and then reused, for example, by re-piercing of the bung by a needle, microbial contamination has occurred on the exposed surfaces of the bung. In such cases, any re-piercing of the bung by a needle may easily transfer the microbial contamination into the vial with subsequent serious complications including morbidity.

Accordingly, it is an object of this invention to provide a vial closure with an exposed surface which remains free of microbial contamination.

It is another object of the invention to reduce the risk of microbial contamination of the contents of a medicament-containing vial which has been sealed with a rubber bung or the like.

It is another object of the invention to avoid contamination of an exposed surface of a bung closing off a medicament containing vial.

Briefly, the invention provides a vial closure which is comprised of a rubber bung having a body portion for sealing an opening in a container and a surface for exposure to a surrounding environment. In addition, the closure includes a contact bactericide permanently disposed on the surface of the bung to be exposed to a surrounding environment.

The contact bactericide is of a type which contains silver as an active ingredient. In addition, the contact bactericide is in the form of a permanent coating on the surface of the bung and particularly, a vapor-deposited coating.

As is known, silver has been used in various forms on medical devices in order to prevent infection and to act as a contact bactericide. For example, U.S. Pat. No. 4,054,139 describes an oligodynamic catheter which is provided with a silver-bearing oligodynamic material on the exterior and interior surfaces in order to prevent bacterial transmission along or within the catheter. Other systems which employ oligodynamic metals in catheters and the like are described in U.S. Pat. Nos. 4,483,688 and 3,699,956.

U.S. Pat. No. 3,396,727 describes the use of a paper coated or impregnated with a bactericidal preventive material, such as oligodynamic silver in a drainage tube environment.

U.S. Pat. Nos. 4,417,892 and 3,848,603 describe other types of antimicrobial substances which can be used in the form of coatings on drainage tubes and catheters.

The provision of a contact bactericide on the exposed surface of the rubber bung serves to prevent microbial growth. As a result, the bung can be employed as a closure or stopper in the opening of a container, such as a glass vial containing medicament. In such cases, the bung can be pierced several times, for example, by a hollow needle in order to access medicament from within the vial without an invasion of contamination from the surface of the bung into the contents of the vial.

The invention further provides the combination of a container for a medicament wherein the container has an opening at one end and a bung disposed in the opening of the container to seal the container. As above, the bung has a contact bactericide disposed on a surface which is exposed to the environment and which is to be pierced by a needle. In addition, a cap may be disposed over the bung while being secured to the container in order to secure the bung in the container and to maintain the surface of the bung in a sealed state. In such an embodiment, a removable means is provided on the cap for exposing the bactericide-containing surface of the bung upon removal of this means from the cap. For example, the removable means may be in the form of a pull tab.

The cap may be made of any suitable material with aluminum being the typical material used. In such cases, the aluminum cap is provided with suitable score lines or the like so as to facilitate the removal of the pull tab.

The container may be filled with any suitable medicament and sealed by means of the bung. Thereafter, the sealed container may be subjected to a conventional steam sterilizing process with or without the cap secured in place. In this regard, the heat and pressure of such a sterilizing process does not affect the integrity of the contact bactericide.

When the container is to be used, the pull tab can be removed thereby exposing the bactericide-containing surface of the bung. Should the user accidentally touch or brush against the exposed surface, the bactericide will prevent contamination of the surface. Further, piercing of the bung by a needle so as to obtain access to the medicament within the container can be repeated over a period of time as the bactericide will prevent contamination of the exposed surface of the bung during this time. As a result, the risk of any possible contamination of the medicament over a period of time is substantially reduced.

The bactericide ensures that any surface contamination associated with the surrounding environment will not result in a contaminated bung surface. Should gross contamination occur, such as by spilling of a large quantity of microbial-latent fluid on the bung which can be readily seen, a simple wipe is sufficient to reduce the thickness of the contaminated layer sufficiently that the bactericide coated surface can take effect and eliminate the instantaneous spillage which is adjacent to the bung material.

In a related way, it has been found that if two rubber bungs or other type of membrane surfaces are brought together for a period of time with one surface being coated with the bactericide then both surfaces tend to be anti-microbial. These two surfaces may then be pierced, for example, in a manner as described in U.S. Pat. No. 5,290,254 to effect a sterile transfer without the need to pre-swab the surfaces of the bung or membranes.

The contact bactericide may be formed on the bung in any suitable fashion. However, at the present time, the preferred technique for forming a coating of the contact bactericide is that as used by Spire Corporation of Bedford, Mass. in applying a SPI-ARGENT™ actively sterile coating. Basically, this is an ion beam assisted deposition process wherein a vapor of atoms is generated and deposited on a substrate, which, in the present case, is a rubber bung.

These and other objects and advantages of the invention will become more apparent from the following detailed description taken in conjunction with the accompany drawings wherein.

Figure 1:
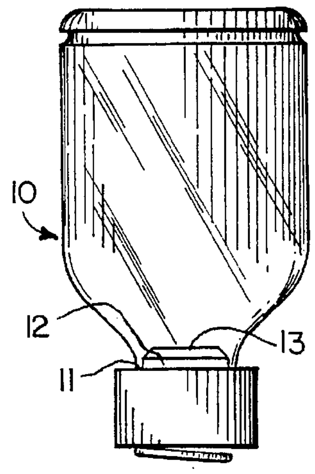
FIG. 1 illustrates a vial of medicament having a bung and cap in accordance with the invention.
Figure 2:
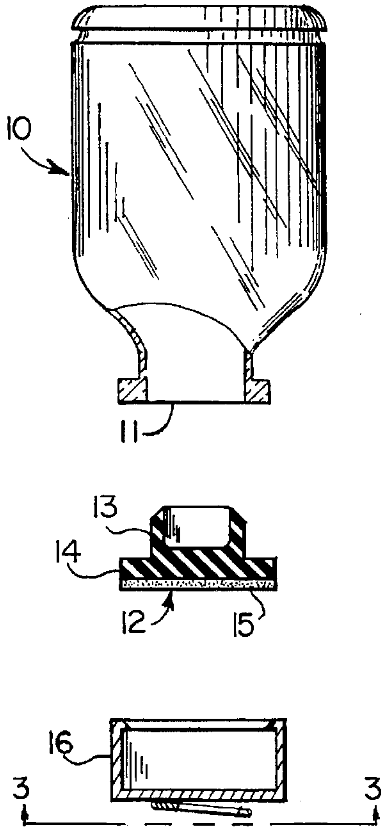
FIG. 2 illustrates an exploded view of the vial of FIG. 1.

Referring to FIGS. 1 and 2, a container 10, such as a glass parenteral vial of conventional structure, is provided for containing a medicament and has an opening 11 at one end. In this respect, the container 10 is shown in an upside down manner as this would be the typical manner in which the container is placed when in use.

In some cases, the glass container 10 may be mounted in a frame (not shown) so as to be suspended. For example, an eyelet or hook can be provided on the bottom side of the container 10 so that the container 10 may be suspended in a vertical manner from a suitable support.

A bung 12, such as a rubber bung, is disposed in the opening of the vial 10 in order to seal the medicament (not shown) within the vial. As indicated in FIG. 2, the bung 12 has a cylindrical body portion 13 for sealing the opening 11 in the container 10 as well as a cap portion 14 with a surface for exposure to the surrounding environment when the bung 12 is in place in the container 10. In this respect, the body portion 13 is suitably sized so as to be fitted into the opening 11 of the container 10 in a friction-fit manner to seal the contents of the container 10 therein.

A contact bactericide 15 is disposed on the exposed surface of the cap portion 14 of the bung 12. This contact bactericide 15 contains silver as an active ingredient and is in the form of a permanent coating on the surface of the bung 12, for example, having been vapor-deposited thereon. For example, the coating is applied by an ion beam assisted deposition process as employed by Spire Corporation.

The bactericide 15 is applied to a thickness sufficient to prevent microbial growth on the exposed surface of the bung 12. In this respect, the bactericide coating is sufficient to prevent contamination of the surface of the bung 12 by a brush type contamination or any similar accidental touch of the bung by a user. The thickness of the treatment which includes penetration of the rubber bung below the surface is up to three (3) microns. The coating (the treatment) and the surface of the rubber bung is very minimal, perhaps 10% and 20% of the treatment thickness. The lower limit of treatment is at least one (1) micron.

A cap 16, for example, of aluminum is disposed over the bung 12 in sealing relation while being secured to the container 10 so as to secure the bung 12 in the container 10 and to maintain the surface of the bung 12 in a sealed state. In this respect, any conventional type of cap may be used.

Figure 3:
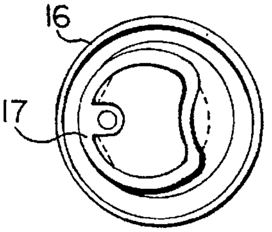
FIG. 3 illustrates a view of the cap taken on line 3—3 of FIG. 2.

Referring to FIGS. 1 and 3, a removable means 17 is provided on the cap 16 for exposing the surface of the bung 12 upon removal of the removable means 17 from the cap 16. For example, the removable means 17 is in the form of a pull tab. As indicated in FIG. 3, the pull tab 17 is of a size and shape so that when removed from the cap proper, a relatively large surface of the bung 12 is exposed to view. Typically, the exposed surface area is sufficient for a user to pierce a needle (not shown) or the like through the bung 12 into the interior of the glass vial 10 to obtain access to the medicament. For example, where the medicament is a liquid, a dose of the liquid medicament can be withdrawn through the needle, for example, into a syringe or other type of structure.

Alternatively, where the medicament is in powder form or the like which requires the addition of a liquid in order to become activated, the needle which pierces through the bung 12 may be used to inject fluid into the vial in order to activate the medicament. After removal of the needle, a second needle, for example, from a syringe can be employed to withdraw the activated medicament.

Despite the need to pierce and re-pierce the bung 12, the bactericide coating remains to prevent microbial growth and/or contamination of the surface of the bung 12. Thus, the risk of any contamination passing into the interior of the vial 10 is reduced.

Figure 4:
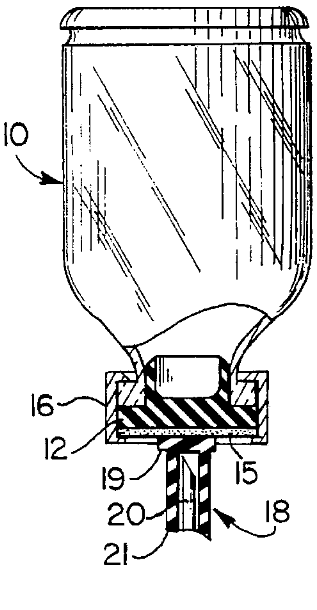
FIG. 4 illustrates a cross-sectional view of the vial of FIG. 1 in contact with an assembly having a sealed needle for piercing the bung of the vial in accordance with the invention.

Referring to FIG. 4, wherein like reference characters indicate like parts as above, the sealed vial 10 may be used with an assembly 18 having a membrane 19 for contacting the exposed surface of the bung after removal of the pull tab 17 and a needle 20 for movement through the membrane 19 and bung 12 in order to access a medicament in the vial 10. Such an assembly 18 may be one, such as described in U.S. Pat. No. 5,290,254. In such an embodiment, after the pull tab 17 has been removed from the cap 16 so as to expose the surface of the bung 12, the membrane 19 of the assembly 18 is abutted against the bung 12 in surface-to-surface contact. This contact is then maintained for a period of time sufficient to make both surfaces anti-microbial. In this respect, it has been found that when the surfaces are brought together for a short period of time, the surface of the membrane tends to become anti-microbial. The needle 20 may then pierce through the membrane 19 and bung 12 to effect a sterile transfer without the need to pre-swab the surface of the membrane 19.

The period of time of contact is dependent on the concentration of bacteria, thickness and medium at which the bacteria resides. However, it has been shown that this type of treatment will reduce the bacteria concentration by five (5) logs in a one hour period. In other words, if the initial concentration of bacteria is $10^8$, after one hour, the concentration will be $10^3$. Approximately 99,999,000 bacteria will have been killed in that time interval. When a person just "brushes" the bung, the bacteria concentration is minimal perhaps about 100–1,000 cfu (colony forming units). The silver treatment would eliminate this level in seconds to perhaps a minute. In the specific example given with low levels of initial bacteria on the uncoated bung, and close proximity contact to eliminate the thickness factor, total anti-microbial activity should be seen in seconds to a few minutes.

The assembly 18 also has a suitable collapsible tube 21 which extends from the membrane 19 and which encloses the needle 20 in a sterile manner. Hence, when the needle 20 pierces through the membrane 19 into the bung 12 of the vial 10, the tube 21 collapses so that the membrane 19 slides along the length of the needle 20. When the needle 20 is removed from the bung 12, the collapsible tube 21 expands and biases the membrane 19 away from the needle 20 so as to again seal the needle 20 within the tube 21.

The contact bactericide 15 is applied on the surface of the bung 12 in a manner so that the bactericide is not compromised or destroyed during sterilization of the contents of the vial 10. In this respect, the bactericide becomes integrated or embedded in the surface of the bung 12 rather than simply being adhered to the bung 12. Thus, the coating of the bactericide is one which does not dissipate under heat and pressure. Further, after sterilization, the coating cannot be removed by wiping. In this respect, it is known that adherent coatings of silver nitrate will dissipate under heat and pressure and can be removed by wiping after sterilization.

Typically, steam sterilization is carried out at temperatures in the range of from 240° F. to 260° F. and at pressures of from 2 to 3 atmospheres. Hence, some of the characteristics of the contact bactericide coating which distinguish this coating from the previously known adherent coatings are the permanence of the coating and the resistance of the coating to heat and pressure.

The invention thus provides a bung with a contact bactericide coating of permanent nature which prevents microbial growth.

The invention further provides a sealed vial of medicament which has a bung which can be exposed for penetration of a needle into the interior of the vial to obtain access to the medicament while maintaining the sterility of the medicament against microbial invasion.

The invention further provides a vial which can be used several times over a period of time without the risk of microbial growth on the exposed surface of the bung closing off the interior of the vial.

What is claimed is:

1. A vial closure comprising a rubber bung having a body portion for fitting in and sealing an opening in a container in a friction fit manner and a surface for exposure to a surrounding environment; and a contact bactericide permanently disposed on said surface.

2. A vial closure as set forth in claim 1 wherein said contact bactericide contains silver as an active ingredient.

3. A vial closure as set forth in claim 1 wherein said contact bactericide is in the form of a permanent coating on said surface of said bung.

4. A vial closure as set forth in claim 1 wherein said contact bactericide is in the form of a vapor-deposited coating on said surface of said bung.

5. In combination a container for a medicament, said container having an opening at one end;

a bung disposed in said opening of said container to seal said container;

a contact bactericide permanently disposed on an exposed surface of said bung;

a cap disposed over said bung and secured to said container to secure said bung in said container and to maintain said surface of said bung in a sealed state; and removable means on said cap for exposing said bactericide containing surface of said bung upon removal of said means from said cap.

6. The combination as set forth in claim 5 wherein said contact bactericide contains silver as an active ingredient.

7. The combination as set forth in claim 5 wherein said contact bactericide is in the form of a permanent coating on said surface of said bung.

8. The combination as set forth in claim 5 wherein said contact bactericide is in the form of a vapor-deposited coating on said surface of said bung.

9. The combination as set forth in claim 5 wherein said cap is made of aluminum.

10. The combination as set forth in claim 9 wherein said removable means is a pull tab.

11. The combination as set forth in claim 9 wherein said bung is made of rubber.

12. The combination as set forth in claim 5 which further comprises a needle for piercing said bung through said exposed bactericide containing surface after removal of said removable means.

13. The combination as set forth in claim 1 which further comprises an assembly having a membrane for contacting said exposed surface of said bung after removal of said removable means and a needle for movement through said membrane and said bung to access a medicament in said container.

14. In combination, a glass parenteral vial containing a medicament and having an opening at one end;

a rubber bung disposed in said opening of said vial to seal said medicament within said vial;

a contact bactericide disposed on an exposed surface of said bung;

a cap disposed over said bung and secured to said container to secure said bung in said container and to maintain said surface of said bung in a sealed state; and removable means on said cap for exposing said bactericide containing surface of said bung upon removal of said means from said cap.

15. The combination as set forth in claim 14 wherein said contact bactericide contains silver as an active ingredient.

16. The combination as set forth in claim 14 wherein said contact bactericide is in the form of a permanent coating on said surface of said bung.

17. The combination as set forth in claim 14 wherein said contact bactericide is in the form of a vapor-deposited coating on said surface of said bung.

18. The combination as set forth in claim 14 which further comprises an assembly having a membrane for contacting said exposed surface of said bung after removal of said removable means and a needle for movement through said membrane and said bung to access a medicament in said container.

* * * * *